US 11,154,252 B2

United States Patent
Meriheinä et al.

(10) Patent No.: US 11,154,252 B2
(45) Date of Patent: Oct. 26, 2021

(54) EARLY ACUTE FALL RISK DETECTION

(71) Applicant: MURATA MANUFACTURING CO., LTD., Nagaokakyo (JP)

(72) Inventors: Ulf Meriheinä, Söderkulla (FI); Pekka Kostiainen, Helsinki (FI)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 259 days.

(21) Appl. No.: 14/617,295

(22) Filed: Feb. 9, 2015

(65) Prior Publication Data

US 2015/0223761 A1 Aug. 13, 2015

(30) Foreign Application Priority Data

Feb. 10, 2014 (FI) ..................................... 20145128

(51) Int. Cl.
*A61B 5/00* (2006.01)
*A61G 7/10* (2006.01)
(Continued)

(52) U.S. Cl.
CPC .......... *A61B 5/7275* (2013.01); *A61B 5/0205* (2013.01); *A61B 5/1115* (2013.01);
(Continued)

(58) Field of Classification Search
CPC ..... A61B 5/746; A61B 5/0205; A61B 5/1115; A61B 5/1116; A61B 5/1117; A61B 5/6801; A61B 5/6891; A61B 5/7275; A61B 2562/0219; A61B 5/021; A61B 5/1126; A61G 7/0527; A61G 7/1065; A61G 7/108; A61G 2203/42; A61G 2203/44
(Continued)

(56) References Cited

U.S. PATENT DOCUMENTS

2006/0281979 A1* 12/2006 Kim ...................... A61B 5/1112
600/301
2007/0157385 A1* 7/2007 Lemire ................ A61G 7/0509
5/600
(Continued)

FOREIGN PATENT DOCUMENTS

CN 1809315 A 7/2006
CN 101151636 A 3/2008
(Continued)

OTHER PUBLICATIONS

Sprangers, R. L., et al. "Initial blood pressure fall on stand up and exercise explained by changes in total peripheral resistance." Journal of Applied Physiology 70.2 (1991): 523-530 (Sprangers).*
(Continued)

*Primary Examiner* — Christian Jang
*Assistant Examiner* — Mitchell E Alter
(74) *Attorney, Agent, or Firm* — Squire Patton Boggs (US) LLP

(57) ABSTRACT

A monitoring system and method for early detection of fall risk. A rise-state of a subject occupying a bed is detected. In response to the detection of the rise-state, blood pressure measurement of the subject is triggered. An alarm when the measured blood pressure is not within a selected range of blood pressures.

9 Claims, 2 Drawing Sheets

(51) Int. Cl.
*A61B 5/11* (2006.01)
*A61G 7/05* (2006.01)
*A61B 5/0205* (2006.01)
*A61B 5/021* (2006.01)

(52) U.S. Cl.
CPC ........... *A61B 5/1116* (2013.01); *A61B 5/1117* (2013.01); *A61B 5/6801* (2013.01); *A61B 5/6891* (2013.01); *A61B 5/746* (2013.01); *A61G 7/0527* (2016.11); *A61G 7/108* (2013.01); *A61G 7/1065* (2013.01); *A61B 5/021* (2013.01); *A61B 5/1126* (2013.01); *A61B 2562/0219* (2013.01); *A61G 2203/42* (2013.01); *A61G 2203/44* (2013.01)

(58) Field of Classification Search
USPC ........................................................ 600/485
See application file for complete search history.

(56) References Cited

U.S. PATENT DOCUMENTS

| | | | | |
|---|---|---|---|---|
| 2009/0012409 | A1* | 1/2009 | Roenneberg | A61B 5/022 600/485 |
| 2010/0298656 | A1* | 11/2010 | McCombie | A61B 5/6824 600/301 |
| 2011/0046498 | A1 | 2/2011 | Klap et al. | |
| 2011/0066008 | A1 | 3/2011 | Banet et al. | |
| 2012/0089419 | A1* | 4/2012 | Huster | A61B 5/1115 705/3 |
| 2012/0172764 | A1* | 7/2012 | Hatlestad | A61B 5/02405 600/595 |
| 2013/0174345 | A1* | 7/2013 | Leu | A47C 21/00 5/694 |
| 2013/0338727 | A1* | 12/2013 | Mokelke | A61N 1/3606 607/45 |

FOREIGN PATENT DOCUMENTS

| | | |
|---|---|---|
| JP | 2008-289664 A | 12/2008 |
| JP | 2010-099383 A | 5/2010 |
| JP | 2011-072371 A | 4/2011 |
| JP | 2012-086013 A | 5/2012 |
| JP | 2012-183199 A | 9/2012 |
| TW | 200933538 A | 8/2009 |
| TW | 201114408 A | 5/2011 |
| TW | M452747 U | 5/2013 |
| WO | 01/75834 A1 | 10/2001 |
| WO | WO 02/41771 A1 | 5/2002 |
| WO | WO 2010/135518 A1 | 11/2010 |

OTHER PUBLICATIONS

Bustamante, Paul, et al. "In-bed Patients Behaviour Monitoring System." Biocomputation, Bioinformatics, and Biomedical Technologies, 2008. BIOTECHNO'08. International Conference on. IEEE, 2008 (Bustamonte).*
International Search Report dated May 6, 2015 corresponding to International Patent Application No. PCT/IB2015/050904.
Finnish Search Report dated Oct. 10, 2014 corresponding to Finnish Patent Application No. 20145128.
Chinese Search Report issued in corresponding Chinese Patent Application No. 201580007564.0 dated Apr. 25, 2018.
Chinese Search Report corresponding to Application No. 201580007564.0, dated Dec. 19, 2018.
Taiwanese Search Report corresponding to Application No. 104103701, dated Sep. 9, 2018.

* cited by examiner

EARLY ACUTE FALL RISK DETECTION

BACKGROUND

1. Field

Embodiments of the present invention relate to a monitoring system and method for early detection of fall risk of a subject.

2. Description of the Related Art

When a person stands up, blood vessels respond to gravity by narrowing. This compensation ensures a steady supply of oxygenated blood to the brain. Orthostatic hypotension, also called as postural hypotension, is a condition where compensatory mechanisms to increase blood pressure are delayed and may result in dizziness and even falls.

For elderly and physically weakened people a fall often occurs as a result of such lowered brain blood pressure when standing up. Fall accidents of elderly or otherwise weakened people result in a lot of suffering and high health care costs. Therefore detection of fall risk situations is very important.

In an existing system, a mat that includes pressure sensors is placed by the bed of a patient, and used to detect if the patient stands up. The mat detects when the patient places his feet thereon, and in order to avoid a possible risk of a fall, alarms the healthcare workers that a patient is getting out of the bed.

A problem with a separate mat placed by the bed is the possible risk of tripping on it. Furthermore a separate mat complicates cleaning of the floor, which is an important aspect especially in hospitals. Another problem with this type of device is also that it will send out an alarm for anyone stepping on it, notwithstanding whether the stepper is a patient, or whether the patient is dizzy and in a risk of falling or not.

SUMMARY

An object of the present invention is to provide an improved solution for detecting a fall risk of a subject getting out of bed. The objects of the present invention are achieved with a monitoring system, a bed, a method, and a computer program product according to the claims.

Embodiments of the present invention use a combination of bed occupancy and position sensing and blood pressure sensing. The detection includes detecting whether a subject occupying a bed intends to get up and then detecting whether the blood pressure of the subject responds appropriately for the subject to safely stand up.

Further advantages of the invention are discussed in more detail with the following embodiments.

BRIEF DESCRIPTION OF THE DRAWINGS

In the following the invention will be described in greater detail, in connection with various embodiments, with reference to the attached drawings, in which.

DETAILED DESCRIPTION

The following embodiments are exemplary. Although the specification may refer to "an", "one" or "some" embodiment(s), this does not necessarily mean that each such reference is to the same embodiment(s), or that the feature only applies to a single embodiment. Single features of different embodiments may be combined to provide future embodiments.

In the following, features of the invention will be described with a simple example of a system and method for detection of a fall risk in which various embodiments of the invention may be implemented. Only elements relevant for illustrating the embodiments are described in detail. Various implementations of, for example, blood pressure measurement and inclination detection are generally known to a person skilled in the art and may not be specifically described herein.

Figure 1:
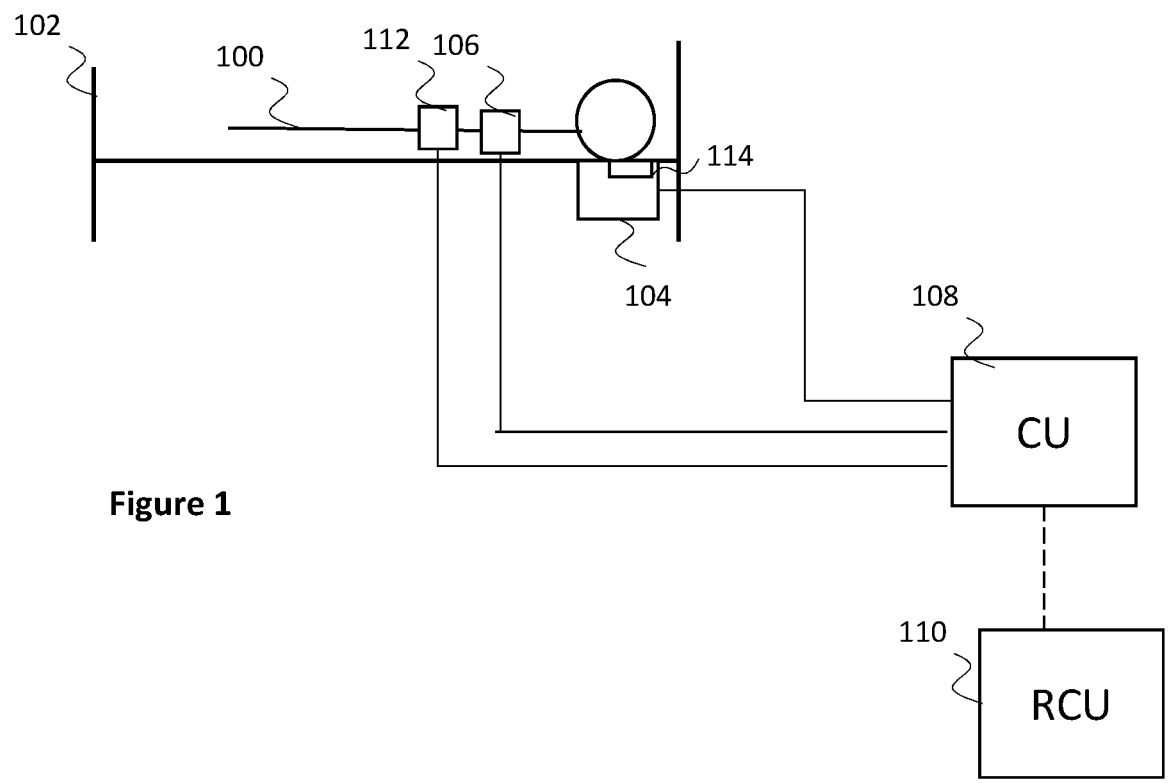
FIG. 1 illustrates basic elements applied in a monitoring system.

The schematic presentation of FIG. 1 illustrates basic elements applied in embodiments of the invention. Embodiments of the invention are related to a monitoring system that includes devices or means for detecting a rise state of a subject, devices or means for measuring blood pressure of the subject, and devices or means for inducing an alarm.

Typically the subject is a human subject 100 schematically shown in FIG. 1. The invention is, however, applicable to any type of subjects that have a heart and blood circulation, and are able to get up from a rest position; thus also to some animal species.

The monitoring system is advantageously applied with a bed 102, meaning a structure where the subject can safely reside, and from which the subject can get up at one's own will. The term bed refers here thus to any type of structure in which the subject can rest without exerting himself, typically supported against gravity. Advantageously, the bed provides a horizontal plane suitable for lying down. The bed may also include a construction that is at least partly tiltable i.e. where at least one end can be tilted or lifted so that the person in the bed rests in a sitting or half-sitting position. Examples of beds include pieces of furniture with a frame and mattress, hospital equipment, stretchers, bunks, and the like.

The monitoring system is configured to be applied with the bed to monitor the subject. The monitoring system may thus include one or more separate elements fixedly or detachably coupled to the bed, or included as an integral part of the bed. Embodiments of the invention thus include also a bed that includes at least part of the elements of the monitoring system.

When the subject 100 rests in the bed 102, the system is configured to detect a bed occupancy state. Bed occupancy has been monitored already in some conventional monitoring systems, and any of those known methods may be applied within the scope. For example, it is possible to place one or more pressure sensors to positions under the subject, and detect the bed occupancy state in response to signals from those pressure sensors.

The exemplary embodiment of FIG. 1 shows a new advantageous method of detecting bed occupancy with an inclinometer 104 attached to the bed. When the subject is in the bed, his heart pumps blood in cyclic contractions through a network of arteries and veins. This myocardial activity of the heart causes mechanical movements of the body of the subject. These movements induce motion in the bed, and this bed motion can be detected with an accelerometer or a special accelerometer for inclination measurement (inclinometer). Bed occupancy can thus be detected with minimal equipment. The same accelerometer or inclinometer can even be used to detect also the rise state of the subject, as will be discussed later on.

As long as the subject rests in the bed, he can toss and turn, but all in all, he can be considered to be safe. When he decides to get up, he has to move in a specific way in the bed. In embodiments of the invention, a specific set of detected motion is interpreted to indicate that the subject intends to get out of the bed, i.e. to indicate rise state of the subject. Whenever this set of motion is detected, the monitoring system deems that the subject has transferred to a rise state.

The rise state may be detected directly from a sensor attached to the subject. For example, the means for detecting a rise state may include an altimeter 106 attached to the upper body part (head, shoulder, etc.) of the subject. A reference level of the altimeter may be set to the level of the horizontal plane of the bed. Before the subject can get up, he has to sit up. When he sits up in the bed, the height of the altimeter changes accordingly. In this example, a motion used for identifying the rise state is thus increase in the detected height from the reference level, and the rise state may be detected when the increase exceeds a specific threshold.

Alternatively, the rise state may be detected indirectly from movement of the bed along with movement of the subject. For example, the means for detecting a rise state may include a MEMS inclinometer 104 connected to the bed 102 to detect changes in inclination of it. For modelling purposes, the subject may be considered as a center of gravity of an object on the bed. When a subject lies in the bed, the center of gravity in the bed is located centrally in relation to the sides of the bed, and closer to the head end of the bed in a longitudinal direction (direction of a length dimension of the horizontal plane of the bed). When the subject sits up, the head and the upper body are lifted up, and the center of gravity moves toward the foot end of the bed. This changes the longitudinal inclination of the bed. On the other hand, when the subject moves toward a side of the bed and moves his legs over the side of the bed, the center of gravity in the bed moves toward the side of the bed. This changes bed inclination in the transverse direction. As an example, the rise state may be detected from detected motion of the bed, here by detecting successively change in a longitudinal inclination and a change in the transverse inclination.

The means for detecting the rise state may include one or more sensors. As discussed earlier, the rise state may be detected with an accelerometer or inclinometer applied for detection of the bed occupancy state. For example, it has been detected that recoil of the body to the heartbeat of the subject tends to vibrate the bed in the longitudinal direction. This vibration may be detected in 0.5 . . . 3 Hz frequency band—typically about 60 beats per minute—with an advanced inclinometer. The sensor used in the bed may preferably be a low noise sensor, with a low signal to noise ratio e.g. 20-30 µG/√Hz, such as the SCA100T inclinometer of Murata™. A sensor like this can detect a ballistocardiologic signal, and also changes in inclinations of merely fractions of degrees of an angle. The amplitude of the vibration is of the order of ~1 mg (g stands for the Earth's standard acceleration due to gravity), and typically the ballistocardiological signal of the vibration requires amplification before further analog-to-digital conversion. The same sensor may be used to detect longitudinal and/or transverse inclinations caused by movements of the subject. Typically the motion signal is not amplified in order to avoid saturation. The SCA100T is a dual-axis inclinometer, which allows detection of inclinations in longitudinal and transversal directions.

It is noted that the invention is not, however, limited to any specific sensor type or to any number of sensors. One or more sensors can be used separately or in combination in the means for detecting the rise state. In addition, the above described detected motions (sitting up, moving to the side) of the subject provide easily identifiable signal states to be associated to his intention to get up. Other motions and signal states may, however, be applied within the scope.

The system for detecting the rise state may include a sensor unit 104 with one or more sensors, and a control unit 108 communicatively coupled to the sensor unit 104 to input signals for further processing.

The sensor unit 104 represents here a functional element for a system in which rise state of a subject occupying a bed is detected by identifying a specific set of detected motions of the subject or the bed. The sensor unit comprises at least one motion sensor and a support structure 114 for mechanical coupling of the at least one motion sensor to the subject or the bed. The mechanical coupling enables generation of a motion signal that represents a detected motion of the bed or the subject, which detected motion is one of the specific set of detected motions that enable identification of the rise state of the subject from the bed. The sensor unit includes also an interface for transmitting signals of the motion sensor to a control unit of the system.

The sensor unit may be an embedded element where he coupling between the control unit and the sensor unit is electrical, allowing both power supply to the sensor unit, as well as wireline exchange of signals between the sensor unit and the control unit. The sensor unit 104 may, alternatively, be a standalone unit with own power supply and/or radio interface to the control unit. The one or more sensors of the standalone sensor unit may be incorporated into one physical element, or they may be physically separate components that are communicatively coupled to each other or to the control unit for combined use in rise state detection. The sensor unit and control unit may even be implemented as one integrated physical device.

Figure 2:
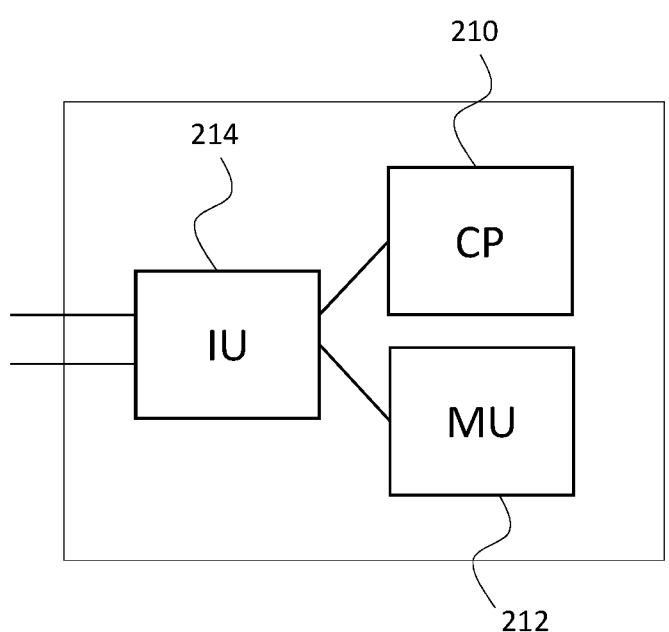
FIG. 2 illustrates functional elements of a control unit.

The control unit 108 represents here another functional element for the system in which rise state of a subject occupying a bed is detected by identifying the specific set of detected motions of the subject or the bed. The block chart of FIG. 2 illustrates in more detail functional elements of the control unit 108. The control unit 108 is a device that may include a processing component 210. The processing component 210 refers to a combination of one or more computing devices for performing systematic execution of operations upon predefined data. The processing component may include one or more arithmetic logic units, a number of special registers and control circuits. The processing component may include or may be connected to a memory unit 212 that provides a data medium where computer-readable data or programs, or user data can be stored. The memory unit may include one or more units of volatile or non-volatile memory, for example EEPROM, ROM, PROM, RAM, DRAM, SRAM, firmware, programmable logic, etc.

The control unit 204 may also include, or be connected to an interface unit 214 that comprises at least one input unit for inputting data to the internal processes of the control unit, and at least one output unit for outputting data from the internal processes of the control unit.

If a line interface is applied, the interface unit 214 typically includes plug-in units acting as a gateway for information delivered to its external connection points and for information fed to the lines connected to its external connection points. If a radio interface is applied, the interface unit 214 typically includes a radio transceiver unit, which includes a transmitter and a receiver. A transmitter of the radio transceiver unit may receive a bitstream from the processing component 210, and convert it to a radio signal for transmission by an antenna. Correspondingly, the radio signals received by the antenna may be led to a receiver of the radio transceiver unit, which converts the radio signal into a bitstream that is forwarded for further processing to the processing component 210. Different line or radio interfaces may be implemented in one interface unit.

The interface unit 214 may also include a user interface with a keypad, a touch screen, a microphone, or equals for inputting data and a screen, a touch screen, a loudspeaker, or equals for outputting data to a user of the device. The user interface may be applied to output a triggered alarm.

The processing component 210, the memory unit 212, and the interface unit 214 are electrically interconnected to provide means for performing systematic execution of operations on the received and/or stored data according to predefined, essentially programmed processes. These operations include the procedures described herein for the control unit of the monitoring system of FIG. 1.

Returning to FIG. 1, the sensor unit 104 and the control unit 108 of FIG. 1 may be included in a local node by the bedside of the subject. In addition, the local node may be communicatively connected to a remote node 110. The remote node 110 may be, for example, an application server that provides a monitoring application and generates related alarms as a service to one or more users. Alternatively, the remote node may be a computing device into which a monitoring application has been installed. The local node may be a dedicated device or combination of devices including the sensor unit and the control unit coupled together as described above. Alternatively, at least part of the local node may be implemented as a portable or wearable sensor unit that interfaces a client application in a dedicated or multipurpose computer device (for example a mobile phone, a portable computing device, or network terminal of a user). A client application in the computer device may interface the sensor unit and a server application. The server application may be available in the control unit 108, a physical remote node 110, or in a cloud of remote nodes accessible through a communication network.

While various aspects of the invention may be illustrated and described as block diagrams, message flow diagrams, flow charts and logic flow diagrams, or using some other pictorial representation, it is well understood that the illustrated units, blocks, apparatus, system elements, procedures and methods may be implemented in, for example, hardware, software, firmware, special purpose circuits or logic, a computing device or some combination thereof. Software routines, which may also be called as program products, are articles of manufacture and can be stored in any apparatus-readable data storage medium, and they include program instructions to perform particular predefined tasks. Accordingly, embodiments of this invention also provide a computer program product, readable by a computer and encoding instructions for monitoring a subject in a device or a system described herein.

As discussed earlier, the fall risk is greatest at the moment when the subject stands up. To reduce the risk, the system is configured to detect the rise state of the subject, and in response to the detected rise state, trigger measurement of blood pressure of the subject. The means for measuring blood pressure 112 of the subject may include any device that generates one or more output values that represent detected characteristics of arterial pressure waves of the subject. These values may be used as such, or be further processed to indicate blood pressure information of the user. During each heartbeat, blood pressure varies between a maximum (systolic) and a minimum (diastolic) pressure. A traditional non-invasive way to measure blood pressure has been to use a pressurized cuff and detect the pressure levels where the blood flow starts to pulsate (cuff pressure falls below diastolic pressure) and where there is no flow at all (cuff pressure exceeds systolic pressure). However, it has been seen that users tend to consider the measurement situations, as well as the pressurized cuff tedious and even stressing, especially in long-term monitoring.

Advantageously, blood pressure of a person in the rise state could be measured with a pressure pulse sensor. The pressure pulse sensor refers here to a device that includes at least one pressure sensor detachably attached to, for example, the arm or wrist of a user and a processing element that transforms signals from the pressure sensor to output values. The configuration is unnoticeable, simple and very easily calibrated, still it provides very accurate results. A sensor of this kind may give, for example, beat to beat times and resulting heart rate as well as blood pressure pulse height and other pulse pressure data. This data may be used as such to determine the need for alarms. The data may also be used to compute systolic and diastolic pressures, which are then used to determine the need for alarms.

Figure 3:
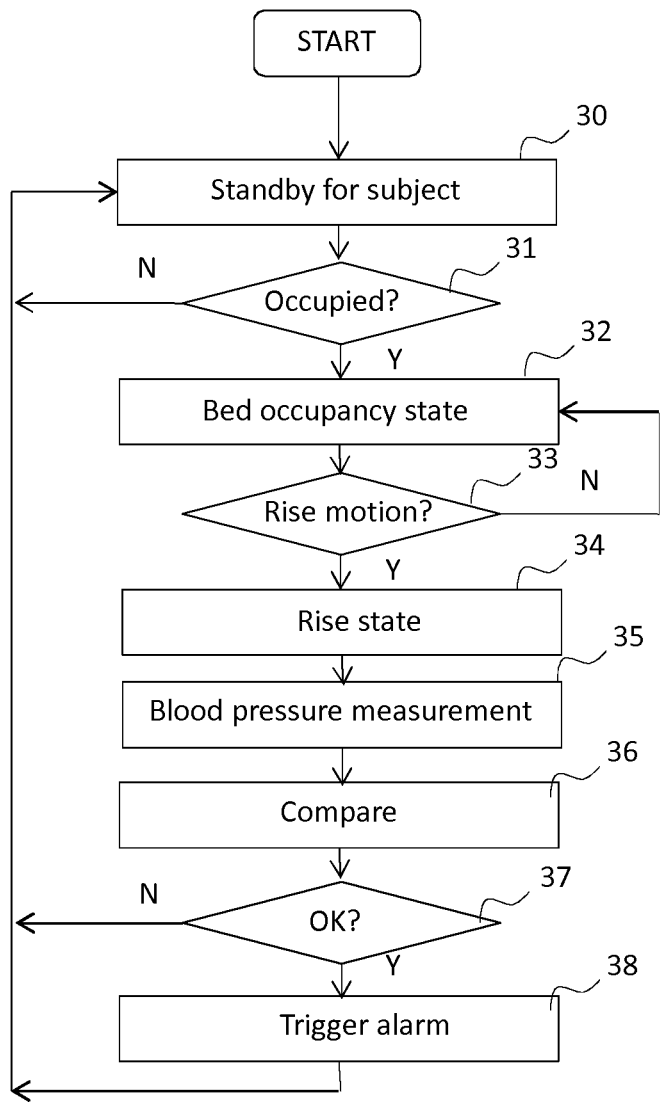
FIG. 3 is a flow diagram illustrating a method for early detection of a fall risk of a subject.

FIG. 3 is a flow diagram illustrating a method to be implemented in the system of FIG. 1. More details on the system may be referred from descriptions of FIGS. 1 and 2. The process begins at a state where the system is installed and switched on and thereafter standby (stage 30) to receive signals from sensors attached to the subject and/or the bed. At first it is checked (stage 31) whether the bed is occupied or not. FIG. 1 illustrated an example, where this bed occupancy information was advantageously determined from ballistocardiological signals acquired with an inclinometer attached to the bed. As long as the bed is unoccupied, the system may remain standby for action.

As soon as the bed is occupied, a bed occupancy state is detected (stage 32) and monitoring indications for the rise state may begin. If specific rise motion is detected, in this example from motions the subject or from longitudinal and/or transversal motions the bed (stage 33), a rise state is detected (stage 34), and blood pressure measurement is triggered (stage 35). One or more blood pressure measurement values (measured values, or values computed from measured values) are compared (stage 36) to one or more specific threshold values (stage 36). The one or more threshold values stand for a selected range of blood pressures, and the comparison indicates whether a compared pressure measurement value is within the selected range of blood pressures or not. Typically the selected range of blood pressures relates to pressures that are estimated to allow the subject to stand up from a lying or sitting position without significantly increased risk of fall. If the measured values are acceptable, no alarm is necessary, the subject may stand up, and the system may return to the standby state (stage 30). If the values are not acceptable, an alarm is triggered (stage 38). After the alarm, the process may return to the standby state or the rise state. This means that if the subject does not stand up, the blood pressure will be measured and the alarm repeated, until the blood pressure reaches acceptable values.

The control unit giving the alarm may be implemented as a small device that may be worn by the subject. It may be adapted to alarm the subject of the risk of a fall by an audio signal. Advantageously, the alarm may be output from a wearable device that includes the pressure pulse element for measuring the blood pressure. Alternatively or additionally, the control unit giving the alarm may be a separate device that may, for example, be attached to the bed or set up in another suitable place close to the bed.

Another alternative is an arrangement where the alarm is additionally or exclusively directed to a member of staff in, for example, a hospital or a residential home. This is a viable option for subjects who may not be able to react to an alarm themselves. Such subjects may be patients suffering from, for example, dementia or Alzheimer's.

The threshold values used in comparisons for triggering the alarm may be predetermined values stored in the system. Alternatively, pre-set adaptive thresholds reflecting personal variations may be applied. For example, sensors of the human body called baroreceptors are located in the three major arteries, the aorta and the two carotid arteries. These sensors detect a drop in blood pressure, when the subject stands up from a sitting or lying position. A difference dp reflects the difference in hydrostatic pressure between sensors in the blood pressure measurement point where carotid arteries are situated.

$$dp = p(\text{measured sitting up}) - p0(\text{lying down, measured over a period of time})$$

where p0 is a normal blood pressure of the subject measured when lying down (bed occupancy state) and p is a normal blood pressure measured when sitting up (rise state). The term normal means here that in either of the states the subject is in normal condition and able to get up without increased risk of fall.

Depending on the subject, the drop is slowly or quickly compensated by the cardiovascular system and the autonomic nervous system of the subject. Also the effect of the difference varies from subject to subject. If the blood pressure sensor is positioned in the wrist, the compensation for both the diastolic and systolic pressure should typically be of the order of 30 to 35 mmHg. It is possible to set an individual threshold for, for instance, the sum of diastolic and systolic pressures to the range of 15 to 30 mmHg. It is preferable to use e.g. the sum of diastolic and systolic pressures as threshold parameter as the sum is less sensitive to random measurement errors. Other measured data (for example pulse rate data) may be combined with the systolic and diastolic pressure values for adaptive thresholds.

The invention provides a monitoring system and a method by which a significant improvement can be achieved by reducing fall risk of subjects. The arrangements according to the present invention are easy and economical to realize and reliable in use.

It should be noted that the foregoing examples of the embodiments of the invention are not intended to restrict the scope of the invention to the specific forms presented above but the present invention is meant rather to cover all modifications, similarities and alternatives which are included in the of the present invention, as defined by the appended claims. All additional embodiments, modifications and applications obvious to those skilled in the art are thus included within the spirit and scope of the invention as set forth by the claims appended hereto.

The invention claimed is:

1. A monitoring system, comprising:
a sensor unit including a motion sensor comprising an inclinometer, and a support structure configured to enable mechanical coupling of the motion sensor to a bed, wherein the mechanical coupling enables the inclinometer to generate a motion signal that represents inclinations of the bed caused by movements of a subject occupying the bed;
a control unit;
an interface between the motion sensor and the control unit, configured to transmit the motion signal to the control unit;
the control unit being configured to:
receive the motion signal from the motion sensor;
detect from the motion signal a specific set of longitudinal or transversal inclinations of the bed or a specific set of longitudinal and transversal inclinations of the bed;
in response to identifying the specific set of inclinations of the bed, detect a rise state of the subject occupying the bed, the rise state indicating that the subject intends to get out of the bed;
trigger, in response to the detection of the rise state from the specific set of inclinations of the bed, blood pressure measurement of the subject;
compare a blood pressure measurement value measured in the rise state to at least one threshold value for a selected range of blood pressures that allow the subject to stand up from a lying or sitting position without increased risk of fall; and
induce an alarm when the blood pressure measurement value measured in the rise state is not within the selected range of blood pressures.

2. The monitoring system according to claim 1, wherein the control unit is included in a local node.

3. The monitoring system according to claim 1, wherein the control unit is included in a remote node.

4. The monitoring system according to claim 1, wherein the control unit is configured to detect the rise state of the subject from a successive combination of a signal representing longitudinal inclination of the bed and a signal representing transversal inclination of the bed.

5. The monitoring system according to claim 1, wherein the threshold value is a predefined value stored in the control unit.

6. The monitoring system according to claim 1, wherein the threshold value comprises a pre-set value input for the subject to the control unit.

7. A bed comprising the sensor unit of claim 1 and a structure in which the subject can rest supported against gravity without exerting himself.

8. A method for detecting fall risk of a subject, said method comprising:
mechanically coupling a motion sensor comprising an inclinometer to a bed, wherein the mechanical coupling enables the inclinometer to generate a motion signal that represents inclinations of the bed caused by movements of a subject occupying the bed;
transmitting the motion signal from the motion sensor to the control unit;
detecting in the control unit from the motion signal a specific set of longitudinal or transversal inclinations of the bed or a specific set of longitudinal and transversal inclinations of the bed;
in response to identifying the specific set of inclinations of the bed, detecting a rise state of a subject occupying a bed, the rise state indicating that the subject intends to get out of the bed;
triggering, in response to the detection of the rise state, blood pressure measurement of the subject;
comparing a blood pressure measurement value measured in the rise state to at least one threshold value for a selected range of blood pressures that allow the subject to stand up from a lying or sitting position without increased risk of fall; and inducing an alarm when the blood pressure measurement value measured in the rise state is not within the selected range of blood pressures.

9. A computer program product, comprising a non-transitory computer-readable medium and readable by a computer, and encoding instructions for executing the method of claim 8.

\* \* \* \* \*